(12) United States Patent
Komuro et al.

(10) Patent No.: US 8,147,720 B2
(45) Date of Patent: *Apr. 3, 2012

(54) LATENT CURING AGENT

(75) Inventors: Katsuhiko Komuro, Tochigi (JP); Masahiko Ito, Tochigi (JP); Daisuke Masuko, Tochigi (JP)

(73) Assignees: Sony Corporation, Tokyo (JP); Sony Chemical & Information Device Corporation, Tokyo (JP)

( * ) Notice: Subject to any disclaimer, the term of this patent is extended or adjusted under 35 U.S.C. 154(b) by 392 days.

This patent is subject to a terminal disclaimer.

(21) Appl. No.: 12/223,869

(22) PCT Filed: Dec. 27, 2007

(86) PCT No.: PCT/JP2007/075136
§ 371 (c)(1),
(2), (4) Date: Aug. 12, 2008

(87) PCT Pub. No.: WO2008/090719
PCT Pub. Date: Jul. 31, 2008

(65) Prior Publication Data
US 2009/0152504 A1    Jun. 18, 2009

(30) Foreign Application Priority Data
Jan. 24, 2007    (JP) ................................. 2007-014187

(51) Int. Cl.
*H01B 1/00*    (2006.01)

(52) U.S. Cl. .................. 252/500; 252/182.33; 525/210; 525/342; 525/523; 525/532; 556/170; 556/173

(58) Field of Classification Search .................. 252/500, 252/182.33; 525/210, 342, 523, 532; 556/170, 556/173
See application file for complete search history.

(56) References Cited

U.S. PATENT DOCUMENTS

| 4,322,513 | A | 3/1982 | Wada et al. |
| 4,324,873 | A | 4/1982 | Wada et al. |
| 6,831,117 | B2 | 12/2004 | Matsushima |
| 7,557,230 | B2 * | 7/2009 | Komuro et al. ............... 556/173 |
| 2008/0251757 | A1 | 10/2008 | Yamamoto et al. |

FOREIGN PATENT DOCUMENTS

| JP | A-56-004625 | 1/1981 |
| JP | A-2001-137690 | 5/2001 |
| JP | A-2002-363255 | 12/2002 |
| JP | A-2002-368047 | 12/2002 |

(Continued)

OTHER PUBLICATIONS

Office Action issued in Korean Patent Application No. 2008/7030702; Nov. 5, 2010; with English-language translation.

(Continued)

*Primary Examiner* — Khanh Tuan Nguyen
(74) *Attorney, Agent, or Firm* — Oliff & Berridge, PLC

(57) ABSTRACT

An aluminum chelate-based latent curing agent is provided which can cure a thermosetting epoxy resin at a relatively low temperature in a short period of time. A method for producing such an aluminum chelate-based latent curing agent, whose curing conditions can be relatively easily controlled, is also provided. The aluminum chelate-based latent curing agent is made latent by reacting a silsesquioxane-type oxetane derivative with an aluminum chelating agent in the presence of an alicyclic epoxy compound.

18 Claims, 1 Drawing Sheet

FOREIGN PATENT DOCUMENTS

| | | |
|---|---|---|
| JP | A-2003-013036 | 1/2003 |
| JP | A-2006-131848 | 5/2006 |
| JP | A-2006-131849 | 5/2006 |
| JP | A-2007-211056 | 8/2007 |
| WO | WO 2006/090794 A1 | 8/2006 |
| WO | WO 2006/132133 A1 | 12/2006 |

OTHER PUBLICATIONS

Aug. 30, 2011 Chinese Office Action issued in Chinese Patent Application No. 200780050360.0 (with translation).

Dec. 9, 2011 Taiwanese Office Action issued in Taiwanese Patent Application No. 97101484 (with translation).

* cited by examiner

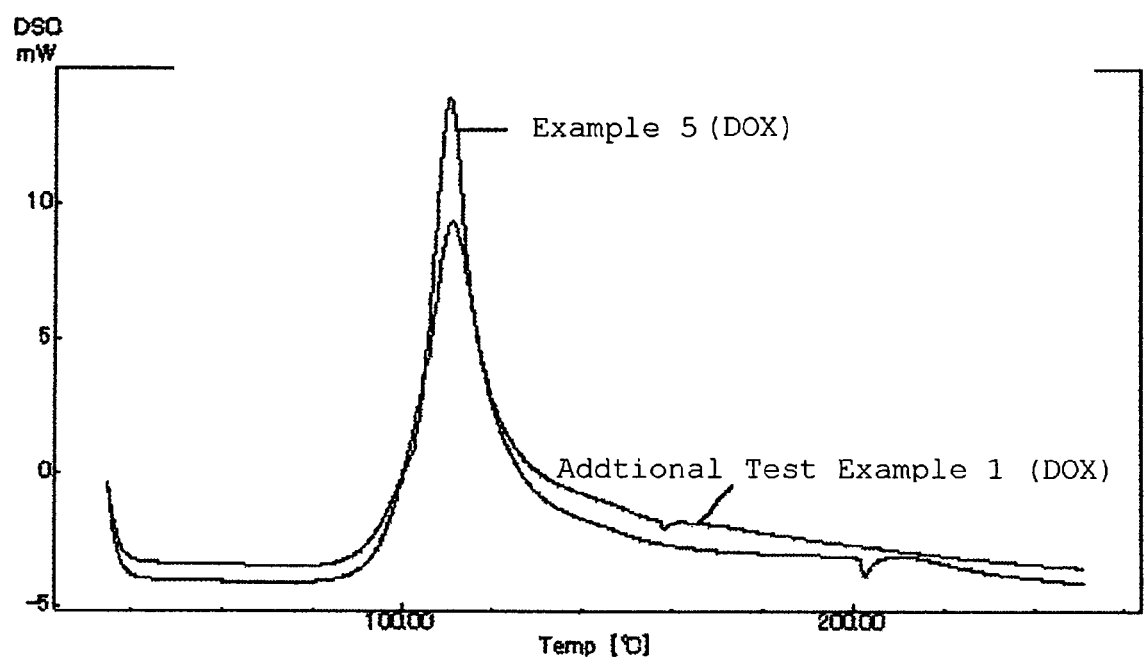

LATENT CURING AGENT

TECHNICAL FIELD

The present invention relates to an aluminum chelate-based latent curing agent which can initiate the curing of a thermosetting composition at a relatively low temperature, a production method thereof, and a thermosetting composition containing the same which has good storage stability.

BACKGROUND ART

Thermosetting resin compositions, such as epoxy resins, are widely used for various adhesion materials, molding materials and the like. One example of a curing agent used for such a thermosetting resin composition is a latent imidazole-based curing agent. Since this latent imidazole-based curing agent does not exhibit a curing performance in a normal storage state, it is widely used to turn thermosetting epoxy resin compositions into a one-component curing composition having good handleability and good storage stability. Representative examples of such a latent imidazole curing agent include microcapsule-type agents which have an epoxy resin cured matter coating the surface of imidazole compound particles which are capable of curing the epoxy resin.

However, such a microcapsule-type latent imidazole curing agent has a coating which is both mechanically and thermally relatively stable. Thus, to initiate the curing reaction, it is necessary to heat to 180° C. or more under pressure. Therefore, there has been the problem that such a microcapsule-type latent imidazole curing agent is not applied to the low-temperature curing type epoxy resin compositions of recent years.

Accordingly, latent curing agents have been proposed which exhibit low-temperature and rapid curability even without the use of a toxic promoter, such as antimony and the like. For example, Patent Document 1 describes a microcapsule-type aluminum chelate-based latent curing agent having a polyvinyl alcohol coating layer formed on the surface of aluminum chelating agent particles (mother particles) which can generate a protonic acid in conjunction with a co-catalyst silanol (silane coupling agent etc.) to cause a cyclic ether (epoxy compound or oxetane compound) to undergo cationic ring-opening polymerization. In Patent Document 1, the polyvinyl alcohol coating layer is formed on the surface of the mother particles by a hybridization method in which polyvinyl alcohol microparticles (daughter particles) having a hydroxyl group, which reacts with the aluminum chelating agent, fuse and stick to the surface of the mother particles. Furthermore, Patent Document 2 describes a microcapsule-type aluminum chelate-based latent curing agent having a coating layer formed on the surface of mother particles. In Patent Document 2, fluorine resin microparticles (daughter particles) which do not have a functional group that can react with the aluminum chelating agent are made to stick to the surface of the mother particles by static electricity, and then the fluorine resin microparticles are fused by a hybridization method to form an integrated surface.

It is noted that details of the curing step for an aluminum chelate-based latent curing agent are described in paragraphs 0007 to 0010 of the above-mentioned Patent Document 1.

[Patent Document 1] Japanese Patent Application Laid-Open No. 2002-368047
[Patent Document 2] Japanese Patent Application Laid-Open No. 2002-363255

DISCLOSURE OF THE INVENTION

Problems to be Solved by the Invention

However, in the case of aluminum chelate-based latent curing agents formed into a microcapsule by utilizing a hybridization method as described in Patent Documents 1 and 2, the microcapsule wall is formed by making the daughter particles collide into the mother particles so as to fuse, or making the daughter particles, which are stuck by static electricity, fuse due to the friction between them. As a result, indents and unevenness tend to occur on the surface, so that there is the problem that stable curing properties cannot be obtained. In addition, it is difficult to control the curing conditions. Furthermore, because the polymerization initiation temperature with respect to the DSC (differential thermal analysis) exothermic peak of a thermosetting epoxy resin composition blended with such a curing agent is too low, it is difficult to say that latency is adequate. Moreover, since an organic solvent (such as toluene, ethyl acetate, MEK and PGMAC) is used during the preparation of a thermosetting composition in which such an aluminum chelate-based latent curing agent is used, the aluminum chelate-based latent curing agent needs to exhibit good solvent resistance.

It is an object of the present invention to solve the problems associated with the above-described conventional techniques, and to provide an aluminum chelate-based latent curing agent which can cure a thermosetting compound at a relatively low temperature in a short time by cationic polymerization, yet which has excellent solvent resistance. It is also an object of the present invention to provide a method for producing an aluminum chelate-based latent curing agent in which the curing conditions can be relatively easily controlled, and to provide a thermosetting composition containing this latent curing agent.

Means for Solving the Problems

The present inventors discovered that a substance obtained as a sediment by reacting an aluminum chelating agent and a silsesquioxane-type oxetane derivative in the presence of an alicyclic epoxy compound in a non-aqueous solvent by heating, could fulfill the above-described objectives, thereby completing the present invention.

Specifically, the present invention provides an aluminum chelate-based latent curing agent which is made latent by reacting a silsesquioxane-type oxetane derivative with an aluminum chelating agent in the presence of an alicyclic epoxy compound.

Furthermore, the present invention provides a method for producing the above-described latent curing agent, the latent curing agent being obtained as a sediment by reacting an aluminum chelating agent and a silsesquioxane-type oxetane derivative in the presence of an alicyclic epoxy compound in a non-aqueous solvent by heating.

Furthermore, the present invention provides a thermosetting composition containing the above-described latent curing agent, a silane coupling agent and a thermosetting compound. Still further, the present invention provides an anisotropic conductive composition in which anisotropic conductive particles are dispersed in this thermosetting composition.

Effect of the Invention

The latent curing agent according to the present invention is made latent by reacting a silsesquioxane-type oxetane derivative with an aluminum chelating agent in the presence of an alicyclic epoxy compound. The latency is thought to be achieved according to the reasons described in the following. Specifically, because the oxetane ring of a silsesquioxane-type oxetane derivative has excellent cationic polymerizability as a result of an ether oxygen thereof having a higher nucleophilicity than an oxirane ring, the oxetane ring undergoes ring-opening polymerization due to the action of the aluminum chelating agent. Furthermore, silanol groups may be formed as a result of some of the alkoxysilyl groups of the polymer being hydrolyzed by the slight amount of moisture present in the polymerization system. Alternatively, in some cases the silanol groups may have been present from the start in the silsesquioxane-type oxetane derivative. These silanol groups interact with the aluminum chelating agent, whereby the aluminum chelating agent is chelated with the polymerized matter. At this stage, along with the ring-opening polymerization of the oxetane ring, epoxy groups in the alicyclic epoxy compound undergo ring-opening polymerization, and are integrated into the polymerized matter along with the aluminum chelating agent. Next, by additionally polymerizing the alicyclic epoxy compound, the polymer of the alicyclic epoxy compound forms a microcapsule wall around the polymerized matter. As a result, a non-aqueous type aluminum chelate-based curing agent is made latent. Therefore, not only can an aluminum chelating agent which is liquid at ordinary temperatures be used as a latent curing agent, but good solvent resistance is also exhibited.

If the microcapsule wall of such a non-aqueous type aluminum chelate-based latent curing agent is dissolved, the latent curing agent can cure a thermosetting compound, such as an epoxy resin or an oxetane compound, at a relatively low temperature in a short time. Furthermore, because this aluminum chelate-based latent curing agent can be produced in a non-aqueous solvent, deactivation can be avoided, whereby deterioration in curing performance can be suppressed.

BRIEF DESCRIPTION OF THE DRAWING

FIG. 1 is a thermal analysis chart of both the aluminum chelate-based latent curing agents of Example 5 (DOX) and Additional Test Example 1 (DOX).

BEST MODE FOR CARRYING OUT THE INVENTION

The latent curing agent according to the present invention is made latent by reacting a silsesquioxane-type oxetane derivative with an aluminum chelating agent in the presence of an alicyclic epoxy compound. Because an aluminum chelating agent which can realize low-temperature, rapid curing is used for this latent curing agent, good low-temperature, rapid curability can be conferred on a thermosetting resin composition blended with this latent curing agent. Furthermore, because it is thought that the aluminum chelating agent is coated by the polymer of the alicyclic epoxy compound, even when this latent curing agent is blended in a thermosetting composition and made into a one-component agent, the storage stability of the thermosetting composition can be greatly improved.

The aluminum chelate-based latent curing agent according to the present invention is a microcapsule having a structure in which a polymer shell of an alicyclic epoxy compound is coated around a core which is a complex of a polymer of a silsesquioxane-type oxetane derivative and an aluminum chelating agent. If this microcapsule agglomerates, the structure may have plural cores scattered in a polymer matrix of the alicyclic epoxy compound. Here, as the polymer of the silsesquioxane-type oxetane derivative, polymers having various degrees of polymerization may be obtained, such as dimers, oligomers or even higher polymers, according to the charged amount of aluminum chelating agent and silsesquioxane-type oxetane derivative, the reaction temperature conditions and the like. However, from the standpoint of particle size control, an oligomer having a degree of polymerization of 10 to 100 is preferable.

The latent curing agent according to the present invention preferably has a spherical shape, and from the standpoint of curing properties and dispersibility, preferably has a particle size of 1 to 10 μm, and more preferably 2 to 3 μm.

Furthermore, if the used amount of the silsesquioxane-type oxetane derivative with respect to the aluminum chelating agent in the aluminum chelate-based latent curing agent according to the present invention is too small, the encapsulation reaction is slowed, while if the used amount is too large, the curing agent solidifies. Thus, with respect to 100 parts by weight of the aluminum chelating agent, the used amount is preferably in the range of from 0.1 to 500 parts by weight, more preferably in the range of from 1 to 500 parts by weight and especially preferably in the range of from 10 to 500 parts by weight. Furthermore, if the used amount of the alicyclic epoxy compound with respect to the sum of the aluminum chelating agent and the silsesquioxane-type oxetane derivative is too small, the agent does not turn into a powder, while if the used amount is too large, the curing properties deteriorate. Thus, with respect to 100 parts by weight of the sum of the aluminum chelating agent and the silsesquioxane-type oxetane derivative, the used amount is preferably in the range of from 0.1 to 1,000 parts by weight, more preferably in the range of from 0.5 to 500 parts by weight and especially preferably in the range of from 1 to 500 parts by weight.

Examples of the aluminum chelating agent in the aluminum chelate-based latent curing agent according to the present invention include complex compounds having three β-ketoenolate negative ions coordinated to aluminum, as represented by the formula (4).

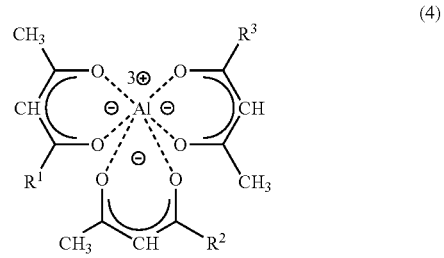

(4)

Here, $R^1$, $R^2$ and $R^3$ each independently represent an alkyl group or an alkoxyl group. Examples of the alkyl group include a methyl group, an ethyl group and the like. Examples of the alkoxyl group include a methoxy group, an ethoxy group, an oleyloxy group and the like.

Specific examples of the aluminum chelating agent represented by the formula (4) include aluminum ethylacetoacetate diisopropylate (ALCH, Kawaken Fine Chemicals Co., Ltd.), aluminum trisethylacetoacetate (ALCH-TR, Kawaken Fine Chemicals Co., Ltd.), aluminum alkylacetoacetate diisopropylate (Aluminum Chelate M, Kawaken Fine Chemicals Co., Ltd.), aluminum bisethylacetoacetate monoacetylacetonate (Aluminum Chelate D, Kawaken Fine Chemicals Co., Ltd.) or aluminum trisacetylacetonate (Aluminum Chelate A(W), Kawaken Fine Chemicals Co., Ltd.).

Examples of the silsesquioxane-type oxetane derivative in the aluminum chelate-based latent curing agent according to the present invention include substances preferably containing 95% or more of the compound represented by formula (1) (OX-SQ-H, Toagosei Co., Ltd.), whose silsesquioxane skeleton is substituted with at least one oxetanyl group which has an oxetane ring. The compound represented by the formula (1), usually, is a pale yellow viscous liquid which has a number average molecular weight of 1,000 to 2,000. This compound dissolves in general-purpose organic solvents, and can easily mix even in epoxy resins and oxetanes. Furthermore, to the extent that the effect of the present invention is not harmed, other oxetane derivatives (for example, a biphenyl-type oxetane derivative; OXBP, Ube Industries, Ltd.) may also be used together with the silsesquioxane-type oxetane derivative.

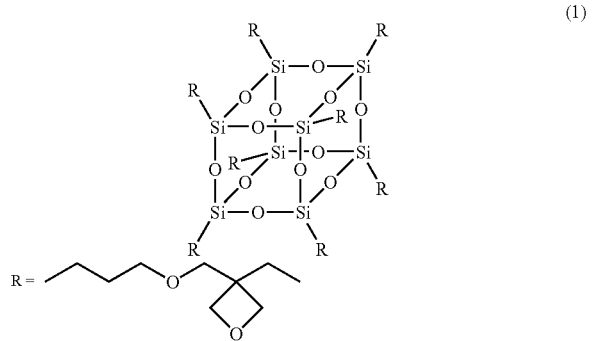

(1)

The silsesquioxane-type oxetane derivative represented by the formula (1) can be easily produced by condensating the alkoxysilyl group of the oxetanyl silane compound represented by the formula (2) (OXT-610, Toagosei Co., Ltd.: boiling point of 125 to 128° C. at 1 mmHg, viscosity of 7 to 8 mPa·s (25° C.)) in the presence of an alkali or an acid in water. As will be described below, this compound represented by the formula (2) can also be used as a silane coupling agent.

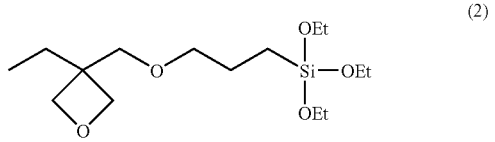

(2)

The alicyclic epoxy compound used in forming the aluminum chelate-based latent curing agent according to the present invention preferably has two or more epoxy groups in one molecule. Examples of such an alicyclic epoxy compound include 3',4'-epoxycyclohexylmethyl 3,4-epoxycyclohexanecarboxylate, 1,2,8,9-diepoxylimonene and the like. Among these, 3',4'-epoxycyclohexylmethyl 3,4-epoxycyclohexanecarboxylate is preferable from the standpoints of reactivity and the ease with which the product can be obtained.

The aluminum chelate-based latent curing agent according to the present invention can be obtained as a sediment by reacting an aluminum chelating agent and a silsesquioxane-type oxetane derivative in the presence of an alicyclic epoxy compound in a non-aqueous solvent by heating, then again adding an alicyclic epoxy compound to the reaction mixture and reacting by heating. If the weight ratio of the alicyclic epoxy compound used in the former part to the alicyclic epoxy compound used in the latter part is comparatively too low, the core becomes unstable, and reactivity decreases, while if that weight ratio is too high, the latent properties of the curing agent deteriorate. Thus, with respect to 1 part by weight in the former part, the latter part is preferably in the range of from 0.1 to 50 parts by weight, and more preferably in the range of from 0.1 to 30 parts by weight.

As the non-aqueous solvent, lower alkyl acetates, such as ethyl acetate and the like, and aromatic solvents, such as toluene and the like, can be preferably used. The heating temperature depends on the kind of solvent and the like, but is usually in the range of from 50 to 200° C., and preferably in the range of from 80 to 200° C. The heating time is usually in the range of from 1 to 3 hours, and preferably in the range of from 1 to 2 hours. The used amount of the non-aqueous solvent can be appropriately selected in consideration of the solubility of the other components and the like. Furthermore, if oxygen is present in the reaction atmosphere, there is a risk of the aluminum chelating agent being deactivated through oxidation. Thus, it is preferable to carry out the reaction in an inert gas atmosphere, for example a nitrogen atmosphere.

The aluminum chelate-based latent curing agent according to the present invention can be obtained by cooling the reaction solution, then filtering the produced sediment, washing the sediment with a poor solvent such as hexane, and drying under reduced pressure. In this case, among the sediment after the reaction has finished, it is preferable to obtain as the aluminum chelate-based latent curing agent which has passed through a filter having a predetermined pore size, for example, a filter made from Teflon® which has a pore size of 8 μm.

The aluminum chelate-based latent curing agent according to the present invention is obtained as microparticles having a primary particle size in the reaction system of from 0.5 to 10 μm by stirring the reaction system using a homogenizer (for example, IKA). However, when removed from the reaction system, the particles tend to turn into secondary particles having a size of from 0.5 to 100 μm. If an anisotropic conductive adhesion coating solution using such a relatively large agglomerated latent curing agent is coated on a substrate, the latent curing agent may become caught in the coating outlet of the coater. In some cases linear patterns (coating stripes) where the coating solution has not been fully coated may form. The occurrence of such coating stripes is an obstacle to realizing a reliable anisotropic conductive connection. Therefore, for relatively large-sized agglomerated secondary particles of the aluminum chelate-based latent curing agent, an operation to pulverize to primary particles is necessary.

When pulverizing, a hammermill, a turbo mill, a roll mill, a jet mill and the like can be used. If a hammermill, a turbo mill or a roll mill is used, there is a risk that the primary particles of the latent curing agent may themselves be destroyed. If a jet mill is used (refer to Japanese Patent Application Laid-Open No. 2001-137690), there is the problem that the pulverizing costs increase, because of the increased size of the apparatus. After the pulverizing is finished, as described above, it is preferable to pass the pulverized matter through a filter having a predetermined pore size.

For this reason, the present inventors carried out research intended to confer an aluminum chelate-based latent curing agent with the quality of not easily agglomerating even if removed from the reaction system. As a result, the present inventors discovered that an aluminum chelate-based latent curing agent obtained by reacting an aluminum chelating agent and a silsesquioxane-type oxetane derivative in the presence of an alicyclic epoxy compound in a non-aqueous solvent by heating, and then further reacting the resultant mixture with an isocyanate compound, hardly agglomerates even if removed from the reaction system. The present inventors further discovered that even if this resultant mixture does agglomerate, the resultant matter can be pulverized to primary particles under extremely mild conditions (for example, the conditions for sedimentation). Especially, the present inventors learned that agglomeration can be dramatically suppressed by reacting with an epoxy compound or an oxetane compound after having reacted with the isocyanate compound.

Furthermore, the present inventors discovered that when reacting an aluminum chelating agent and a silsesquioxane-type oxetane derivative in the presence of an alicyclic epoxy compound in a non-aqueous solvent by heating, an aluminum chelate-based latent curing agent obtained by reacting an epoxy compound or an oxetane compound along with the isocyanate compound also hardly agglomerates even if removed from the reaction system, and even if it does agglomerate, the resultant matter can be pulverized to primary particles under extremely mild conditions (for example, the conditions for sedimentation).

Accordingly, as a preferred embodiment, the present invention provides: (a) an aluminum chelate-based latent curing agent obtained by, after making latent, further reacting with an isocyanate compound; (b) an aluminum chelate-based latent curing agent obtained by, after reacting with an isocyanate compound, further reacting with an epoxy compound or an oxetane compound; and (c) an aluminum chelate-based latent curing agent obtained by reacting with an epoxy compound or an oxetane compound along with an isocyanate compound.

The isocyanate group of the isocyanate compound is believed to react with hydroxyl groups on the surface of the microparticles of the aluminum chelate-based latent curing agent. Therefore, reacting with an isocyanate compound can be thought to be equivalent to carrying out a surface treatment of the aluminum chelate-based latent curing agent using an isocyanate compound. Furthermore, since the epoxy compound or oxetane compound can be considered as essentially not reacting with the isocyanate group of the isocyanate compound, the epoxy compound or oxetane compound are believed to undergo cationic polymerization by the aluminum chelate-based latent curing agent, thereby being fixed on the particle surface.

Here, the isocyanate compound is a polyfunctional isocyanate compound having two or more isocyanate groups in a single molecule. Specific examples include m-phenylene diisocyanate, p-phenylene diisocyanate, 2,4-tolylene diisocyanate, 2,6-tolylene diisocyanate, naphthalene-1,4-diisocyanate and the like. These can be used by diluting with an organic solvent, such as toluene.

If the used amount of the isocyanate compound is too small, the effects of having reacted the isocyanate compound cannot be expected, while if the used amount is too large, the reactivity of the curing agent is reduced. Thus, with respect to 100 parts by weight of the aluminum chelating agent, the used amount is preferably in the range of from 0.1 to 200 parts by weight, and more preferably in the range of from 0.1 to 100 parts by weight.

The epoxy compound is a polyfunctional epoxy compound having two or more epoxy groups in a single molecule. Specific examples include Bis-A type epoxy compounds, such as Epicoat 828 (manufactured by Japan Epoxy Resins Co., Ltd.), Bis-F type epoxy compounds, such as Epicoat 806 (manufactured by Japan Epoxy Resins Co., Ltd.), naphthalene type epoxy compounds, such as HP-4032 (manufactured by Dainippon Ink and Chemicals, Incorporated), alicyclic epoxy compounds, such as CEL2021P (manufactured by Daicel Chemical Industries Ltd.) and the like. Among these, the use of an alicyclic epoxy compound is especially preferable from the standpoint that reactivity is high.

If the used amount of the epoxy compound is too small, the effects of having reacted the epoxy compound cannot be expected, while if the used amount is too large, the reactivity of the curing agent is reduced. Thus, with respect to 100 parts by weight of the aluminum chelating agent, the used amount is preferably in the range of from 0.1 to 300 parts by weight, and more preferably in the range of from 0.1 to 200 parts by weight.

The oxetane compound is a polyfunctional oxetane compound having two or more oxetanyl groups in a single molecule. Specific examples include xylylene-type oxetanes, such as OXT-121 (manufactured by Toagosei Co., Ltd.), silsesquioxane-type oxetanes, such as OX-SQ-H (manufactured by Toagosei Co., Ltd.), ether-type oxetanes, such as OXT-221 (manufactured by Toagosei Co., Ltd.), biphenyl-type oxetanes, such as Etemacoll OXBP (manufactured by Ube Industries, Ltd.), phenol novolac-type oxetanes, such as PNOX-723 (manufactured by Toagosei Co., Ltd.), silicate-type oxetanes, such as OX-SC (manufactured by Toagosei Co., Ltd.) and the like. Among these, the use of xylylene-type oxetanes, biphenyl-type oxetanes and phenol novolac-type oxetanes is preferable from the standpoint that the heat resistance of the cured matter is high.

If the used amount of the oxetane compound is too small, the effects of having reacted the oxetane compound cannot be expected, while if the used amount is too large, the reactivity of the curing agent is reduced. Thus, with respect to 100 parts by weight of the aluminum chelating agent, the used amount is preferably in the range of from 0.1 to 300 parts by weight, and more preferably in the range of from 0.1 to 200 parts by weight.

When reacting the above-described isocyanate compound, epoxy compound or oxetane compound, the reaction can be carried out at the reaction temperature at which the aluminum chelating agent and silsesquioxane-type oxetane derivative were reacted in the presence of an alicyclic epoxy compound in a non-aqueous solvent by heating.

According to the above-described production method of the present invention, the curing properties of the aluminum chelate-based latent curing agent can be controlled by varying the kind and used amount of the silsesquioxane-type oxetane derivative and alicyclic epoxy compound, the kind and used amount of the aluminum chelating agent and reaction conditions. For example, if the reaction temperature is lowered, the curing temperature can be lowered, while conversely, if the reaction temperature is increased, the curing temperature can be increased.

The aluminum chelate-based latent curing agent according to the present invention can be used for the same applications as conventional imidazole-based latent curing agents, and can preferably provide a low-temperature, rapid curing thermosetting composition by using together with a silane coupling agent and a thermosetting compound.

If the used amount of the aluminum chelate-based latent curing agent in the thermosetting composition is too small, the composition does not sufficiently cure, while if the used amount is too large, the resin properties (for example, flexibility) of the cured matter of the composition deteriorate. Thus, with respect to 100 parts by weight of the thermosetting compound, the used amount is preferably in the range of from 1 to 30 parts by weight, and more preferably in the range of from 1 to 20 parts by weight.

The silane coupling agent has a function of initiating cationic polymerization of a thermosetting resin (for example, a thermosetting epoxy resin) in conjunction with the aluminum chelating agent, as described in paragraphs 0010 to 0014 of Japanese Patent Application Laid-Open No. 2002-368047. Furthermore, it is thought that the silane coupling agent has a function of capping hydroxyl groups which are unstable and can become a catalyst poison, thereby stabilizing the reaction system. Such a silane coupling agent has 1 to 3 lower alkoxy groups in the molecule, and may have a group which is reactive to the functional group of the thermosetting resin in the molecule. Examples of such a group include a vinyl group, a styryl group, an acryloyloxy group, a methacryloyloxy group, an epoxy group, an amino group, a mercapto group and the like. Among them, an alicyclic epoxy-type silane coupling agent is especially preferred. Furthermore, since the latent curing agent according to the present invention is a cationic curing agent, a silane coupling agent having an amino group or a mercapto group can be used in cases where the amino group or mercapto group essentially does not capture the produced cation species. In addition, it is preferred to use the alicyclic epoxy type silane coupling agent together with a silane coupling agent which contains an ethoxysilyl group. In such a case, a balance can be attained between exothermic onset temperature and the leading edge peak.

Specific examples of such a silane coupling agent include: vinyltris(2-methoxyethoxy)silane, vinyltriethoxysilane, vinyltrimethoxysilane, 3-styryltrimethoxysilane, 3-methacryloxypropyltrimethoxysilane, 3-acryloxypropyltrimethoxysilane, 3-glycidoxypropyltrimethoxysilane, 3-glycidoxypropylmethyldiethoxysilane, N-2-(aminoethyl)-3-aminopropyltrimethoxysilane, N-2-(aminoethyl)-3-aminopropylmethyldimethoxysilane, 3-aminopropyltriethoxysilane, N-phenyl-3-aminopropyltrimethoxysilane, 3-mercaptopropyltrimethoxysilane, 3-chloropropyltrimethoxysilane and the like. Preferred examples of an alicyclic epoxy type silane coupling agent include 2-(3,4-epoxycyclohexyl)ethyltrimethoxysilane represented by the formula (3).

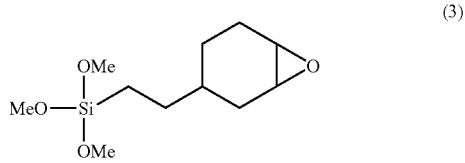

(3)

If the used amount of the silane coupling agent in the thermosetting composition is too small, the composition has low curing properties, while if the used amount is too large, the resin properties (for example, storage stability) of the cured matter of the composition deteriorate. Thus, with respect to 100 parts by weight of the aluminum chelate-based latent curing agent, the content is preferably in the range of from 1 to 1,000 parts by weight, and more preferably in the range of from 50 to 500 parts by weight.

Examples of thermosetting compounds which can be used include thermosetting epoxy resins or compounds, thermosetting urea resins, thermosetting melamine resins, thermosetting phenol resins, oxetane compounds and the like. Among these, if adhesive strength after curing is considered as a beneficial point, thermosetting epoxy resins or compounds can be preferably used.

Such thermosetting epoxy resins or compounds may be in a liquid or a solid state, and preferably have an epoxy equivalent of usually about 100 to 4,000, and two or more epoxy groups in the molecule. Examples which can be preferably used include bisphenol A-type epoxy compounds, phenol novolac-type epoxy compounds, cresol novolac-type epoxy compounds, ester-type epoxy compounds, alicyclic epoxy compounds and the like. In addition, monomers and oligomers are included in these compounds. Among these, from the standpoint of high reactivity, alicyclic epoxy compounds, such as CEL2021P (manufactured by Daicel Chemical Industries Ltd.), can be preferably used.

The oxetane compounds may be in a liquid or a solid state, and preferably have two or more oxetanyl groups in the molecule. Examples which can be preferably used include OXT-121, OXT-221 and OX-SQ-H (manufactured by Toagosei Co., Ltd.). In addition, monomers and oligomers are included in these compounds. Among these, from the standpoint of low reactivity and low ionic impurity concentration, OXT-221, OX-SQ-H and the like can be preferably used.

The thermosetting composition according to the present invention can be produced by uniformly mixing and stirring by an ordinary method the aluminum chelate-based latent curing agent, the silane coupling agent, the thermosetting compound and other additives which may be added as required.

The thus-obtained thermosetting composition according to the present invention has a aluminum chelate-based curing agent which has been made latent, so that despite being a one-component type, the composition has excellent storage stability. Furthermore, the latent curing agent works together with the silane coupling agent so that the thermosetting compound can undergo low-temperature, rapid cationic polymerization.

Moreover, by further blending conductive particles, such as nickel particles, known in the art for anisotropic conductive connection, or a deposited resin film known in the art, such as a phenoxy resin, in the thermosetting composition according to the present invention, the thermosetting composition can be used as an anisotropic conductive composition. If the thermosetting composition is molded into a film, it can be used as an anisotropic conductive film. The kind, particle size and blended amount of the conductive particles, and kind, blended amount and film thickness of the deposited film can be made to have the same structure as known anisotropic conductive pastes or anisotropic conductive films. A representative blend example of the anisotropic conductive paste or film has 8 to 12 parts by weight of aluminum chelate-based latent curing agent, 50 to 80 parts by weight of phenoxy resin, 20 to 50 parts by weight of alicyclic epoxy compound, 5 to 30 parts by weight of epoxy-modified polyolefin, 1 to 20 parts by weight of silane coupling agent and 1 to 20 parts by weight of conductive particles. In addition, a solvent, a monomer for dilution and the like may be appropriately blended as required. Such an anisotropic conductive paste or anisotropic conductive film enables low-temperature, quick connection in about 5 seconds at 150° C., also with low conduction resistance and good adhesion strength.

EXAMPLES

The present invention will now be described in more detail by the following examples.

Example 1

A three-necked flask made from Teflon (registered trademark) equipped with a condenser tube was charged with 177.3 g of kerosene, 9.1 g of 66% solution of an aluminum chelating agent (aluminum ethylacetoacetate diisopropylate; ALCH, manufactured by Kawaken Fine Chemicals Co., Ltd.) in toluene, 9.4 g of 66% solution of a silsesquioxane-type oxetane derivative (OX-SQ-H, Toagosei Co., Ltd.) in toluene, and 4.2 g of 66% solution of an alicyclic epoxy compound (3',4'-epoxycyclohexylmethyl 3,4-epoxycyclohexanecarboxylate (CEL2021P, Daicel Chemical Industries Ltd.) in toluene, and the resultant mixture was stirred for 30 minutes at 140° C. by a homogenizer (13,500 rpm). Next, 8.4 g of 66% solution of CEL2021P in toluene was added dropwise to the reaction mixture (latter addition), and the resultant mixture was stirred for additional 30 minutes at 140° C. by a homogenizer. After the stirring was finished, the reaction mixture was cooled to room temperature using an ice bath, and the mixture was then filtered using a Buchner funnel. The obtained powder was washed 3 times using 100 g of heptane, then dried under reduced pressure to obtain a white powder in a 48% yield as an aluminum chelate-based latent curing agent.

Example 2

A white powder in a 50% yield was obtained as an aluminum chelate-based latent curing agent by repeating the same procedure of Example 1, except that the amount of 66% solution of the CEL2021P in toluene added in the latter addition was changed from 8.4 g to 4.2 g.

Example 3

A white powder in a 60% yield was obtained as an aluminum chelate-based latent curing agent by repeating the same procedure of Example 1, except that the amount of 66% solution of the CEL2021P in toluene added in the latter addition was changed from 8.4 g to 16.8 g.

Example 4

A white powder in a 76% yield was obtained as an aluminum chelate-based latent curing agent by repeating the same procedure of Example 1, except that the stirring time after the latter addition of 66% solution of the CEL2021P in toluene was changed from 30 minutes to 4 hours.

Comparative Example 1

A three-necked flask made from Teflon (registered trademark) equipped with a condenser tube was charged with 177.3 g of kerosene, 9.1 g of 66% solution of an aluminum chelating agent (aluminum ethylacetoacetate diisopropylate; ALCH, manufactured by Kawaken Fine Chemicals Co., Ltd.) in toluene, 9.4 g of 66% solution of a silsesquioxane-type oxetane derivative (OX-SQ-H, Toagosei Co., Ltd.) in toluene, and 4.2 g of 66% solution of an alicyclic epoxy compound (3',4'-epoxycyclohexylmethyl 3,4-epoxycyclohexanecarboxylate (CEL2021P, Daicel Chemical Industries Ltd.) in toluene, and the resultant mixture was stirred by a homogenizer (13,500 rpm) while heating. When the temperature of the reaction mixture reached 140° C., the mixture was cooled to room temperature using an ice bath. Although the mixture was filtered using a Buchner funnel, no solid was obtained.

Comparative Example 2

A quite hard solid was recovered (43%) by repeating the same procedure of Example 1, except that the rotation speed of the homogenizer was changed from 13,500 rpm to 6,500 rpm.

Comparative Example 3

A three-necked flask made from Teflon (registered trademark) equipped with a condenser tube was charged with 177.3 g of kerosene, 10 g of ethyl cellulose, 9.1 g of 66% solution of an aluminum chelating agent (aluminum ethylacetoacetate diisopropylate; ALCH, manufactured by Kawaken Fine Chemicals Co., Ltd.) in toluene, 9.4 g of 66% solution of a silsesquioxane-type oxetane derivative (OX-SQ-H, Toagosei Co., Ltd.) in toluene, and 4.2 g of 66% solution of an alicyclic epoxy compound (3',4'-epoxycyclohexylmethyl 3,4-epoxycyclohexanecarboxylate (CEL2021P, Daicel Chemical Industries Ltd.) in toluene, and the resultant mixture was stirred for 30 minutes at 140° C. by a homogenizer (13,500 rpm). Next, 8.4 g of 66% solution of CEL2021P in toluene was added dropwise to the reaction mixture (latter addition), and the resultant mixture was stirred for additional 30 minutes at 140° C. by a homogenizer. After the stirring was finished, the reaction mixture was cooled to room temperature using an ice bath, and the mixture was then filtered using a Buchner funnel. The obtained powder was washed 3 times using 100 g of heptane, then dried under reduced pressure to obtain a white powder in a 60% yield as an aluminum chelate-based latent curing agent.

Evaluation Test 1

A thermosetting composition was prepared by uniformly mixing, using a stirrer, 0.2 g of the aluminum chelate-based latent curing agent obtained in the above examples and comparative examples, 3.3 g of an oxetane derivative (DOX, Toagosei Co., Ltd.), and 0.8 g of a silane coupling agent (KBE403: KBM303=1:1 (Shin-Etsu Chemical Co., Ltd.)). The resultant composition was subjected to thermal analysis (rate of temperature increase 10° C./min, 35→250° C., under a nitrogen gas flow) using a differential thermal analysis (DSC) apparatus (DSC-60, Shimadzu Corporation) to measure the exothermic onset temperature (° C.), the exothermic peak temperature (° C.) and the gross calorific value (J/g). Furthermore, the degree of agglomeration was visually evaluated. As the evaluation criteria, if no agglomeration was ascertained, an "A" was given, if a slight amount of agglomeration was ascertained, a "B" was given, and if the agglomeration was at a level which would be a problem in practical use, a "C" was given. The obtained results are shown in Table 1. It is noted that in terms of practical use, the preferred ranges for the exothermic onset temperature, the exothermic peak temperature and the gross calorific value are 50 to 98° C., 75 to 125° C. and 250 J/g or more, respectively.

TABLE 1

| Latent curing agent | Agglomeration | Exothermic onset temperature (° C.) | Exothermic peak temperature (° C.) | Gross calorific value (J/g) |
| --- | --- | --- | --- | --- |
| Example 1 | A | 80.7 | 116.4 | 431.6 |
| Example 2 | A | 78.1 | 106.6 | 396.7 |
| Example 3 | A | 88.2 | 110.7 | 443.4 |
| Example 4 | A | 95.3 | 120.9 | 266.2 |
| Comparative Example 1 | — | Solid not obtained | | |
| Comparative Example 2 | C | Sample could not be pulverized. Measurement impossible. | | |
| Comparative Example 3 | B | 80.2 | 113.6 | 350.8 |

From the results of Examples 1 to 4 in Table 1, good exothermic onset temperature, exothermic peak temperature and gross calorific value were shown when the aluminum chelate-based latent curing agent was used which was made latent by reacting a silsesquioxane-type oxetane derivative with an aluminum chelating agent in the presence of an alicyclic epoxy compound. In contrast, in the case of Comparative Example 1, in which latter addition of the alicyclic epoxy compound was not carried out, the aluminum chelate-based latent curing agent could not be powderized at ordinary temperatures, so that latency could not be achieved. In the case of Comparative Example 2, in which the rotation speed of the homogenizer was halved, the polymer particles strongly agglomerated, so that the product could not be used as a latent curing agent. In the case of Comparative Example 3, in which ethyl cellulose was further added as a shell material, this resulted in the opposite effect of causing agglomeration.
Evaluation Test 2

A thermosetting composition was prepared by uniformly mixing, using a stirrer, 0.8 g of the aluminum chelate-based latent curing agent obtained in the above examples and comparative examples, 13.2 g of an oxetane derivative (DOX, Toagosei Co., Ltd.), and 3.2 g of a silane coupling agent (KBE403: KBM303=1:1). The thermosetting composition was prepared in the same manner as that in Evaluation Test 1. Four grams of the resultant composition was placed in a sample bottle, and then 1 g of the solvent shown in Table 2 was further added thereto. After confirming that the mixture was uniform, the sample bottle was placed in a 40° C. oven, and then it was confirmed every 12 hours whether the composition had cured or not. Curing was determined as the point where fluidity was lost. The time required for curing is shown in Table 2.

TABLE 2

| Latent curing agent | Toluene (hr) | Ethyl acetate (hr) | Methyl ethyl ketone (hr) | PGMAC (hr) |
| --- | --- | --- | --- | --- |
| Example 1 | 147 | 25 | 76 | 76 |
| Example 2 | 24 | 24 | 24 | 24 |
| Example 3 | 13 | 13 | 13 | 13 |
| Example 4 | 22 | 22 | 22 | 22 |
| Comparative Example 1 | — | — | — | — |
| Comparative Example 2 | — | — | — | — |
| Comparative Example 3 | <12 | <12 | <12 | <12 |

From the results of Examples 1 to 4 in Table 2, good solvent resistance was shown when the aluminum chelate-based latent curing agent was used which was made latent by reacting a silsesquioxane-type oxetane derivative with an aluminum chelating agent in the presence of an alicyclic epoxy compound. In contrast, in the cases of Comparative Example 1, in which latter addition of the alicyclic epoxy compound was not carried out, and Comparative Example 2, in which the rotation speed of the homogenizer was halved, since they were never possible to use as a latent curing agent, the solvent resistance test was not considered. In the case of Comparative Example 3, in which ethyl cellulose was further added as a shell material, solvent resistance was insufficient.

Example 5

A white powder in a 62% yield was obtained as an aluminum chelate-based latent curing agent by repeating Example 1, except that the reaction was carried out while introducing nitrogen gas into the reaction system. The yield improved to 62% compared with the 48% of Example 1 just by introducing nitrogen gas.

Example 6

A white powder in a 66% yield was obtained as an aluminum chelate-based latent curing agent by repeating Example 2, except that the reaction was carried out while introducing nitrogen gas into the reaction system. The yield improved to 66% compared with the 50% of Example 2 just by introducing nitrogen gas.
Evaluation Test 3

A thermosetting composition was prepared by uniformly mixing, using a stirrer, 0.2 g of the aluminum chelate-based latent curing agent obtained in Examples 5 and 6 and the aluminum chelate-based latent curing agent obtained from the additional tests of Examples 1 and 2, 3.3 g of a matrix (oxetane derivative (DOX, Toagosei Co., Ltd.) or Bis-A type liquid epoxy compound (YL980, Japan Epoxy Resins Co., Ltd.) or an alicyclic epoxy compound (CEL2021P, Daicel Chemical Industries Ltd.)), and 0.8 g of a silane coupling agent (KBE403: KBM303=1:1). The resultant composition was subjected to thermal analysis in the same manner as in Example 1 using a differential thermal analysis (DSC) apparatus (DSC-60, Shimadzu Corporation) to measure the exothermic onset temperature (° C.), the exothermic peak temperature (° C.) and the gross calorific value (J/g). Furthermore, the transparency of the compound was visually evaluated. As the evaluation criteria, cases of extreme transparency were given an "AA" and cases of transparency were given an "A." The obtained results are shown in Table 2. Furthermore, as described above, in terms of practical use, the preferred ranges for the exothermic onset temperature, the exothermic peak temperature and the gross calorific value are 50 to 98° C., 75 to 125° C. and 250 J/g or more, respectively.

TABLE 3

| Latent curing agent | Matrix | Composition transparency | Exothermic onset temperature (° C.) | Exothermic peak temperature (° C.) | Gross calorific value (J/g) |
| --- | --- | --- | --- | --- | --- |
| Example 5 | DOX | AA | 83.8 | 110.0 | 536.8 |
| | YL980 | AA | 89.6 | 126.7 | 41.3 |
| | CEL2021P | AA | 71.8 | 86.4 | 534.0 |
| Example 6 | DOX | AA | 65.3 | 107.2 | 591.4 |
| | YL980 | AA | 80.4 | 105.3 | 47.5 |
| | CEL2021P | AA | 50.1 | 89.5 | 573.1 |
| Additional Test Example 1 | DOX | A | 83.1 | 110.6 | 450.8 |
| | YL980 | A | 78.1 | 103.9 | 33.3 |
| | CEL2021P | A | 55.8 | 76.4 | 452.5 |
| Additional Test Example 2 | DOX | A | 78.1 | 106.6 | 396.7 |
| | YL980 | A | 72.1 | 94.1 | 28.8 |
| | CEL2021P | A | — | — | — |

From Table 3, it can be seen that in Examples 5 and 6, in which the aluminum chelate-based latent curing agent was obtained under a nitrogen flow, the transparency of the compound was higher for all three kinds of used matrix, yet gross calorific value was also higher and activity improved, as compared with Additional Test Examples 1 and 2, in which the aluminum chelate-based latent curing agent was not obtained under a nitrogen flow. The thermal analysis charts for Example 5 (DOX) and Additional Test Example 1 (DOX) are shown in FIG. 1. From this FIGURE, it can be seen that the sharpness of the exothermic peak was improved in Example 5.

Example 7

A three-necked flask made from Teflon (registered trademark) equipped with a condenser tube was charged with 177.3 g of kerosene, 9.1 g of 66% solution of an aluminum chelating agent (aluminum ethylacetoacetate diisopropylate; ALCH, manufactured by Kawaken Fine Chemicals Co., Ltd.) in toluene, 9.4 g of 66% solution of a silsesquioxane-type oxetane derivative (OX-SQ-H, Toagosei Co., Ltd.) in toluene, and 4.2 g of 66% solution of an alicyclic epoxy compound (3',4'-epoxycyclohexylmethyl 3,4-epoxycyclohexanecarboxylate (CEL2021P, Daicel Chemical Industries Ltd.) in toluene, and the resultant mixture was stirred for 30 minutes at 140° C. by a homogenizer (13,500 rpm). Next, 4.0 g of an isocyanate compound (Coronate L45ET, Nippon Polyurethane Industry Co., Ltd.) was charged into the reaction mixture, and the resultant mixture was stirred for additional 30 minutes at 140° C. by a homogenizer. After the stirring was finished, the reaction mixture was cooled to room temperature using an ice bath, and the mixture was then filtered using a Buchner funnel. The obtained powder was washed 3 times using 100 g of heptane, then dried under reduced pressure to obtain 10.5 g of a pale yellow powder (synthesis yield of 62%) as an aluminum chelate-based latent curing agent. Then, 9.4 g of the obtained latent curing agent was dispersed in heptane, and the resultant mixture was filtered with a filter having a pore size of 8 μm. The filtrate was dried to obtain 4.4 g (47%) of an aluminum chelate-based latent curing agent fine powder.

Example 8

8.2 g of a pale yellow powder (synthetic yield of 61%) was obtained as an aluminum chelate-based latent curing agent by repeating Example 7, except that the amount of isocyanate compound (Coronate L45ET, Nippon Polyurethane Industry Co., Ltd.) was changed from 4.0 g to 8.0 g. Then, 10.0 g of the obtained latent curing agent was dispersed in heptane, and the resultant mixture was filtered with a filter having a pore size of 8 μm. The filtrate was dried to obtain 4.7 g (47%) of an aluminum chelate-based latent curing agent fine powder.

Example 9

8.2 g of a pale yellow powder (synthetic yield of 53%) was obtained as an aluminum chelate-based latent curing agent by repeating Example 7, except that the amount of isocyanate compound (Coronate L45ET, Nippon Polyurethane Industry Co., Ltd.) was changed from 4.0 g to 1.0 g. Then, 7.4 g of the obtained latent curing agent was dispersed in heptane, and the resultant mixture was filtered with a filter having a pore size of 8 μm. The filtrate was dried to obtain 3.5 g (47%) of an aluminum chelate-based latent curing agent fine powder.

Evaluation Test 4

The particle size before and after the filtering with a filter having a pore size of 8 μm of the aluminum chelate-based latent curing agents of Examples 7 to 9 was measured using a particle size distribution analyzer manufactured by Sysmex Corporation. Furthermore, a thermosetting composition was prepared by uniformly mixing using a stirrer 0.2 g of the aluminum chelate-based latent curing agent, 3.3 g of a matrix (oxetane derivative (DOX, Toagosei Co., Ltd.)), and 0.8 g of a silane coupling agent (KBE403: KBM303=1:1). The coating properties of the resultant composition were evaluated by a bar coater. Cases where no coating unevenness occurred were given an "A", and a "C" in cases where coating unevenness did occur. The obtained results are shown in Table 4.

TABLE 4

|  |  | Average particle size (μm) | Bar coater coatability |
|---|---|---|---|
| Example 7 | Before filtering | 2.11 | C |
|  | After filtering | 1.79 | A |
| Example 8 | Before filtering | 3.38 | C |
|  | After filtering | 2.88 | A |
| Example 9 | Before filtering | 3.35 | C |
|  | After filtering | 2.33 | A |

From Table 4, it can be seen that by filtering with a filter having a pore size of 8 μm, average particle size decreases and bar coater coating properties also improve.

Example 10

An anisotropic conductive cured composition in the blend of Table 5 was prepared using the aluminum chelate-based latent curing agent of Example 1. The resultant composition was coated to a dry thickness of 20 μm onto a release polyester film, and then dried for 5 minutes at 70° C. to produce an anisotropic conductive film. When FOB pressure-bonding and FOG pressure-bonding were carried out using this anisotropic conductive film for 5 seconds at 150° C., good conduction reliability and connection strength were exhibited. Furthermore, when IC tag pressure-bonding was carried out, using the anisotropic conductive cured composition as an anisotropic conductive paste, for 5 seconds at 150° C., good conduction reliability and connection strength were exhibited.

TABLE 5

| Component | Blended amount parts by weight |
|---|---|
| Aluminum chelate-based latent curing agent of Example 1 | 15 |
| Phenoxy resin (YP50, Tohto Kasei Co., Ltd.) | 50 |
| Alicyclic epoxy resin (CEL2021P, Daicel Chemical Industries Ltd.) | 33 |
| High molecular weight alicyclic epoxy resin (EHPE3150CE, Daicel Chemical Industries Ltd.) | 15 |
| Epoxy-modified polybutadiene (PB3600, Daicel Chemical Industries Ltd.) | 10 |
| Silane coupling agent (KBM303, Shin-Etsu Chemical Co., Ltd.) | 8 |
| Conductive particles (particle size 3.75 μm, AUL, Sekisui Chemical Co., Ltd.) | 19.57 |

INDUSTRIAL APPLICABILITY

The aluminum chelate-based latent curing agent according to the present invention can cure a thermosetting compound at a relatively low temperature in a short period of time, and is thus useful as an adhesion material for electronic materials capable of low-temperature curing.

The invention claimed is:
1. A thermosetting composition comprising:
a silane coupling agent;
a thermosetting compound; and an aluminum chelate-based latent curing agent being made latent by reacting a silsesquioxane-type oxetane derivative with an aluminum chelating agent in the presence of an alicyclic epoxy compound and in the absence of ethyl cellulose, wherein an amount of the silsesquioxane-type oxetane derivative is in a range of 0.1 to 500 parts by weight with respect to 100 parts by weight of the aluminum chelating agent, and an amount of the alicyclic epoxy compound is in a range of 0.1 to 1,000 parts by weight with respect to 100 parts by weight of a total amount of the aluminum chelating agent and the silsesquioxane-type oxetane derivative; wherein the aluminum chelate-based latent is present in an effective amount such that the curing of the thermosetting composition can be initiated at a low temperature, and the thermosetting composition has an exothermic onset temperature in a range of 78.1 to 95.3° C. and an exothermic peak temperature in a range of 106.6 to 120.9° C.

2. The thermosetting composition according to claim 1, wherein the aluminum chelating agent is a complex compound having three β-ketoenolate negative ions coordinated to aluminum.

3. The thermosetting composition according to claim 1, wherein the aluminum chelating agent is aluminum ethylacetoacetate diisopropylate, aluminum trisethylacetoacetate, aluminum alkylacetoacetate diisopropylate, aluminum bisethylacetoacetate monoacetylacetonate or aluminum trisacetylacetonate.

4. The thermosetting composition according to claim 1, wherein the aluminum chelating agent is aluminum ethylacetoacetate diisopropylate.

5. The thermosetting composition according to claim 1, wherein the silsesquioxane-type oxetane derivative includes oxetanylsilsesquioxane represented by the formula (1)

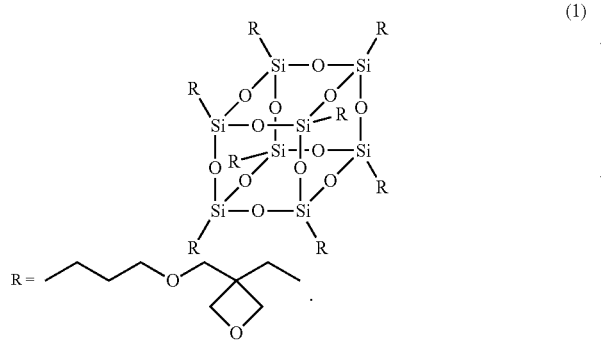

6. The thermosetting composition according to claim 1, wherein the alicyclic epoxy compound is 3',4'-epoxycyclohexylmethyl 3,4-epoxycyclohexanecarboxylate.

7. The thermosetting composition according to claim 1, wherein, after being made latent, the aluminum chelate-based latent curing agent is obtained by further reacting with an isocyanate compound.

8. The thermosetting composition according to claim 7, wherein after reacting with the isocyanate compound, the aluminum chelate-based latent curing agent is obtained by further reacting with an epoxy compound or an oxetane compound.

9. The thermosetting composition according to claim 8, wherein the epoxy compound is a Bis-A type epoxy compound, a Bis-F type epoxy compound, a naphthalene type epoxy compound or an alicyclic epoxy compound.

10. The thermosetting composition according to claim 8, wherein the oxetane compound is a xylylene-type oxetane, a silsesquioxane-type oxetane, an ether-type oxetane, a biphenyl-type oxetane, a phenol novolac-type oxetane or a silicate-type oxetane.

11. The thermosetting composition according to claim 7, wherein, after being made latent, the aluminum chelate-based latent curing agent is obtained by reacting with an epoxy compound or an oxetane compound along with the isocyanate compound.

12. The thermosetting composition according to claim 7, wherein the isocyanate compound is m-phenylene diisocyanate, p-phenylene diisocyanate, 2,4-tolylene diisocyanate, 2,6-tolylene diisocyanate or naphthalene-1,4-diisocyanate.

13. The thermosetting composition according to claim 1, wherein the thermosetting compound is an alicyclic epoxy compound.

14. The thermosetting composition according to claim 1, wherein the thermosetting compound is an oxetane compound.

15. The thermosetting composition according claim 1, wherein the silane coupling agent is an oxetane type silane coupling agent and/or an alicyclic epoxy type silane coupling agent.

16. The thermosetting composition according to claim 15, wherein the oxetane type silane coupling agent is represented by the formula (2)

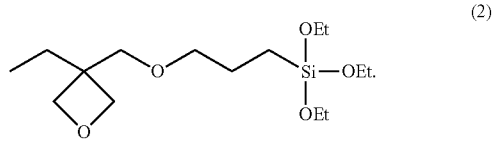

17. The thermosetting composition according to claim 15, wherein the alicyclic epoxy type silane coupling agent is 2-(3,4-epoxycyclohexyl)ethyltrimethoxysilane represented by the formula (3)

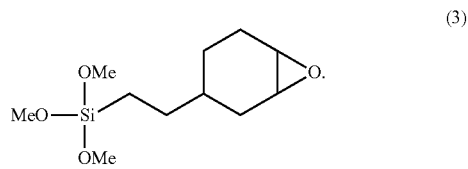

18. An anisotropic conductive composition in which conductive particles are dispersed in the thermosetting composition according to claim 1.